United States Patent
Al Rubh

(10) Patent No.: US 11,207,001 B2
(45) Date of Patent: Dec. 28, 2021

(54) SIGNAL TRANSDUCTION DEVICE

(71) Applicant: Imam Abdulrahman Bin Faisal University, Dammam (SA)

(72) Inventor: Jafar Mohammed Hassan Al Rubh, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 302 days.

(21) Appl. No.: 16/380,045

(22) Filed: Apr. 10, 2019

(65) Prior Publication Data

US 2020/0323465 A1    Oct. 15, 2020

(51) Int. Cl.
*A61B 5/103* (2006.01)
*A61B 5/00* (2006.01)

(52) U.S. Cl.
CPC ............ *A61B 5/1038* (2013.01); *A61B 5/441* (2013.01); *A61B 5/4851* (2013.01); *A61B 5/6807* (2013.01); *A61B 2562/0247* (2013.01)

(58) Field of Classification Search
CPC ..... A61B 5/1038; A61B 5/441; A61B 5/4851; A61B 5/6807; A61B 5/389; A61B 5/7455; A61B 5/7405; A61B 2562/0247
See application file for complete search history.

(56) References Cited

U.S. PATENT DOCUMENTS

| | | | |
|---|---|---|---|
| 6,958,681 B1 | 10/2005 | Sykes, Sr. | |
| 2005/0131317 A1* | 6/2005 | Oddsson | A61B 5/1121 600/592 |
| 2007/0073196 A1 | 3/2007 | Tanaka et al. | |
| 2012/0109013 A1* | 5/2012 | Everett | A61B 5/6807 600/587 |
| 2013/0296741 A1 | 11/2013 | Wiggin et al. | |
| 2015/0216449 A1 | 8/2015 | Fleischer et al. | |
| 2016/0338621 A1* | 11/2016 | Kanchan | G16Z 99/00 |
| 2016/0367191 A1* | 12/2016 | Esposito | A61B 5/11 |

OTHER PUBLICATIONS

Fan, et al. ; A Haptic Feedback System for Lower-Limb Prostheses ; IEEE Transactions on Neural Systems and Rehabilitation Engineering, vol. 16, No. 3 ; Jun. 2008 ; 8 pages.

* cited by examiner

*Primary Examiner* — Sean P Dougherty
*Assistant Examiner* — Alexander H Connor
(74) *Attorney, Agent, or Firm* — Oblon, McClelland, Maier & Neustadt, L.L.P.

(57) ABSTRACT

A device that non-invasively detects objects beneath or around the foot or a foot position and transmits signals which are processed and then output via an output device on a skin surface not affected by a neurological deficit, such as the hands or thighs. This device is suitable for subjects with diabetic neuropathy who have lost sensation in their feet and are at risk of punctures, cuts or other physical damage and at risk of sprains, strains or falls due to lack of an ability to detect objects underfoot and foot position.

17 Claims, 5 Drawing Sheets

SIGNAL TRANSDUCTION DEVICE

BACKGROUND OF THE INVENTION

Field of the Invention

Figure 1:
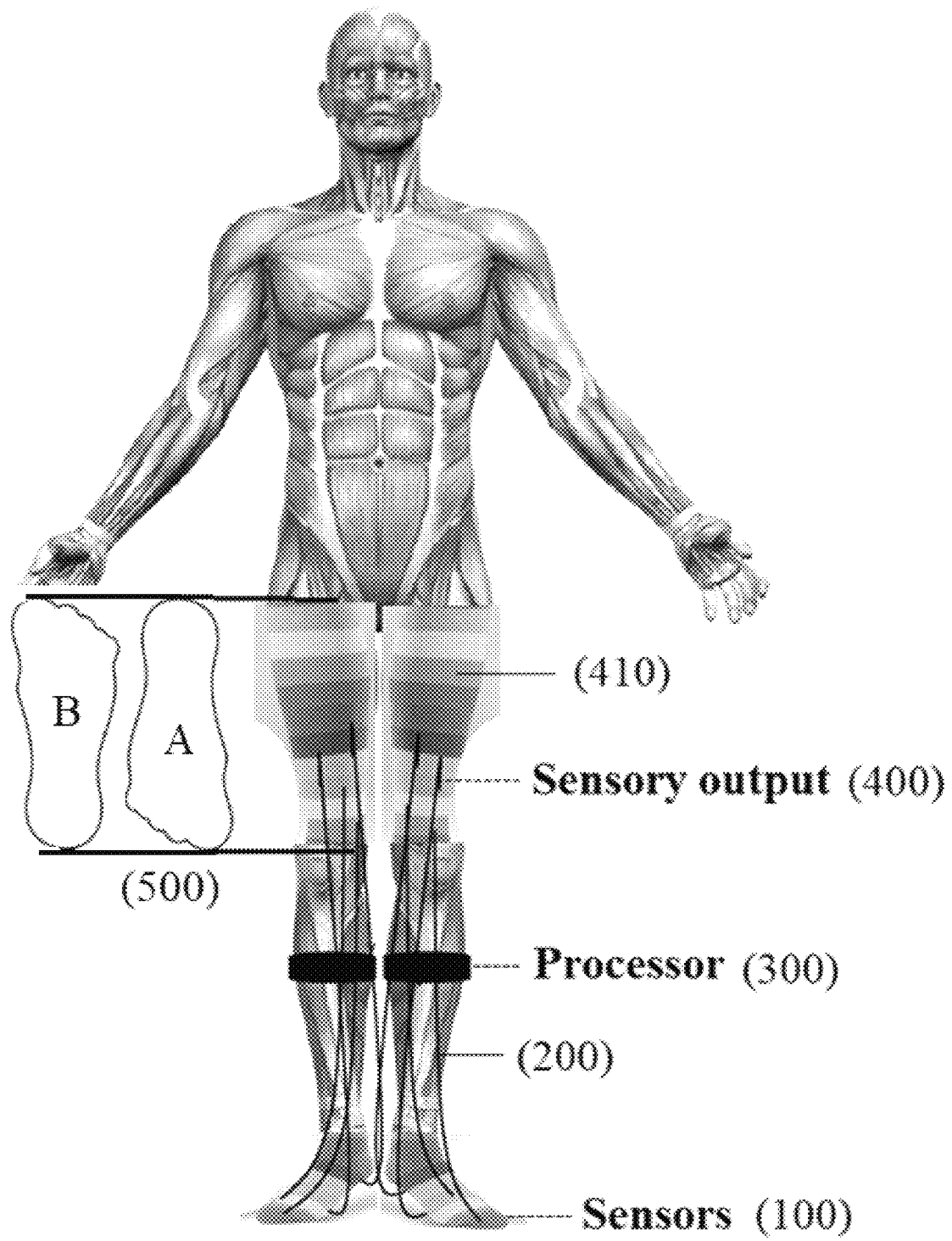

The invention involves the fields of medicine, particularly neurology, physical therapy, and prosthetic devices.

Description of Related Art

Diabetes mellitus is quite common in the population of Saudi Arabia and has a prevalence of about 20-25%. Diabetes mellitus affects bodily metabolism and causes high blood glucose. Chronic levels of high blood sugar can detrimentally affect multiple organs in the body including the nervous system. Dysfunction of the nervous system caused by diabetes mellitus often occurs first in the feet and lower limbs where the affected nerves cannot function properly leading to diabetic neuropathy and loss of sensation. This poses an ongoing risk to a person who has lost sensation because they cannot easily detect sharp objects, blisters and other physical damage to the feet. Moreover, the loss of sensation makes walking difficult and increases the risk of falls. There is an ongoing unsatisfied need for ways to compensate for loss of sensation in feet and lower limbs.

Devices for receiving and emitting signals are known in the field of prosthetic devices. However, these are unsuitable for natural limbs that have lost sensation because they generally require hardwiring or surgical implantation of electrodes into the skin of a person fitted with the prosthetic device. Electrodes have been connected between a non-biological, prosthetic hand and corresponding nerves of the hand, median, radial and ulnar nerves in the mid forearm; Tan, et al., Sci Transl. Med. 6 (257:257ra138, *A neural interface provides long-term stable natural touch perception* (2014). Flat interface nerve electrodes or FINEs were implanted on the median and ulnar nerves and a four-contact spiral electrode was implanted on the radial nerve; see, respectively, Tyler D J, Durand D M. *Chronic response of the rat sciatic nerve to the flat interface nerve electrode*. Ann Biomed Eng. 2003; 31:633-642; and Naples G G, Mortimer J T, Scheiner A, Sweeney J D. *A spiral nerve cuff electrode for peripheral nerve stimulation*. IEEE Trans Biomed Eng. 1988; 35:905-916. Other work involved the use of somatosensory prosthetics built with neural interfaces that provide somatosensory feedback between prosthesis and nerves of the hand, median, ulnar and radial nerves; Tyler, et al., (2015). Other research has been directed to myoelectric prostheses which stimulate peripheral nerves using implanted cuff electrodes proportional to forces on the thumb, index and middle fingers of a prosthetic hand; Schiefer, et al. (2016). For example, an artificial hand attached to intrafascicular electrodes implanted into the stumps of median and ulnar nerves has been used to provide object discrimination in patients with upper limb amputation; see Horch K, Meek S, Taylor T G, Hutchinson D T. *Object discrimination with an artificial hand using electrical stimulation of peripheral tactile and proprioceptive pathways with intrafascicular electrodes*. IEEE Trans Neural Syst Rehabil Eng. 2011; 19:483-489. Fan, et al., Transactions of Neural Systems and Rehabilitation Engineering 16: 270 (2008) describe a haptic feedback system for lower-limb prosthesis.

As mentioned above, the methods described above are used with artificial, non-biological prosthetic hands and not with natural limbs that have lost sensation, such as the feet of a subject with diabetic neuropathy. For a subject who has not lost a limb and who does not need a prosthetic foot or leg it is undesirable to invasively implant electrodes directly into the skin as this leads to irritation, discomfort, pain and infection.

Some work has been performed with non-prosthetic devices. Sykes, U.S. Pat. No. 6,958,681, describes an electrical device that has a push button switch mounted on the heel of a shoe connected to a vibrator on a leg to provide a signal when a foot is in contact with a surface. Fleischer, et al., U.S. Patent Pub. 2015/0216449 describes a wireless sensor for detecting and monitoring pressure on a body part. Wiggin, et al., U.S. 2013/029674.1 describe ankle-foot orthotic devices with vibrotactile feedback. Tanaka, et al., U.S. 2007/0073196, describe a device for applying sensory stimulation to skin. As apparent from prior work, a new system or device that provides higher quality output information in an easy to perceive sensory form to subjects who have lost sensation in their feet and lower limbs is needed. In view of the above, the inventors developed a system that provides information that accurately maps conditions at different positions on the foot or lower limb and permits a use to sense these inputs on a part of the body not impaired by neurological map can take the same shape and orientation of the foot parts thus allowing a user to distinguish the exact site of sensor input on the foot which is output as a sensation on the thigh. In addition to that the user can feel the different types of sensation modalities, as sharp or dull sensation, cold or heat, thus preventing damage from environmental hazards underneath the user's feet. Also, the device may notify the patient by alarm for mispositioning the foot so that the now aware patient can prevent falls or pressure ulcers. The device can surround the whole foot so that it may feel the size of shoes for example and other sensations.

In view of these differences and limitations on prior technologies, the inventor sought to develop a safe, non-invasive system to permit subjects with peripheral neuropathy in the feet to restore sensation, thus permitting a patient to again perceive dangerous objects and precarious foot positions.

BRIEF SUMMARY OF THE INVENTION

The invention involves a device and system for compensating for loss of sensation in the feet and lower limbs associated with diabetic neuropathy and similar conditions. It uses pressure sensors as well as sensors measuring other important parameters placed on the feet and lower limbs to receive information and relay it via a processor to output devices positioned on the thighs or another skin surface that has not loss sensation. The output devices are arranged in a way to facilitate understanding of the tactile output signals, for example, by mapping and corresponding input sensor locations to corresponding locations on the thighs or other body surface. This system includes sensors to receive signals that the feet and lower limbs of a subject receive poorly or not at all due to neurological dysfunction, a processor for receiving, sorting, transducing or amplifying these signals, and output devices which produce tactile signals on a body part not affected by the neurological dysfunction, such as on the thighs of a subject wearing or otherwise equipped with the system. In contrast to existing systems for artificial prosthetics, the system of the invention does not require its input sensors or to be implanted into the body and does not require replacement of a natural limb with a prosthetic device. Rather, sensors can be adhered to the skin or integrated into clothing in a manner that positions the input sensors over body parts lacking sensation and positions output devices over non-dysfunctional body parts that can receive tactile sensations. For example, it may be incorporated into one or more stretchable garments that cover the feet and lower limbs and thighs or into interconnected garments such as socks or shoes containing input sensors connected via wires or in some embodiments, wirelessly, to output devices in clothing positioned over the thigh. The terms "system" and "device" may be used interchangeably, however, in some embodiments a "device" may describe physically-connected input sensors, processor(s) and output devices and a "system" can describe these elements (or additional ancillary elements) in which at least one connection is a remote or wireless connection.

BRIEF DESCRIPTION OF THE SEVERAL VIEWS OF THE DRAWING(S)

FIG. 1 describes one configuration of the system of the invention with input pressure sensors (100) positioned over the feet, connected via wires or cables (200) to a processor (300) positioned on the calf, and output devices (400) on the thighs. Output devices may be configured within a foot-shaped area of the thigh (500) to correlate with placement of input sensors on the foot. In this embodiment, the system is integrated by means of wires conduct signals between the components and the output devices are arranged in a series of horizontal stripes which receive signals from different sensors (100) on the feet. Position of virtual foot containing output devices: toe downward (A), toe upward (B).

Figure 2:
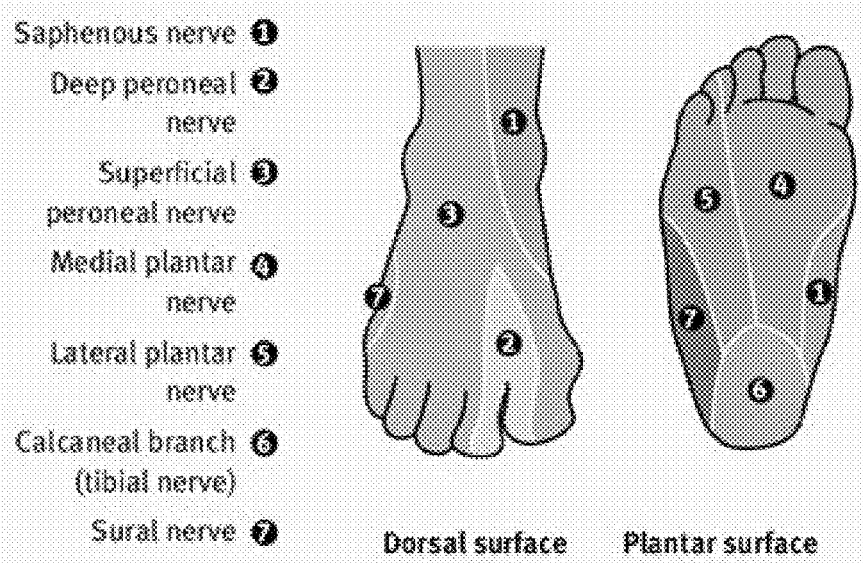

FIG. 2. Dorsal and plantar foot surfaces on which sensors may be placed.

Figure 3:
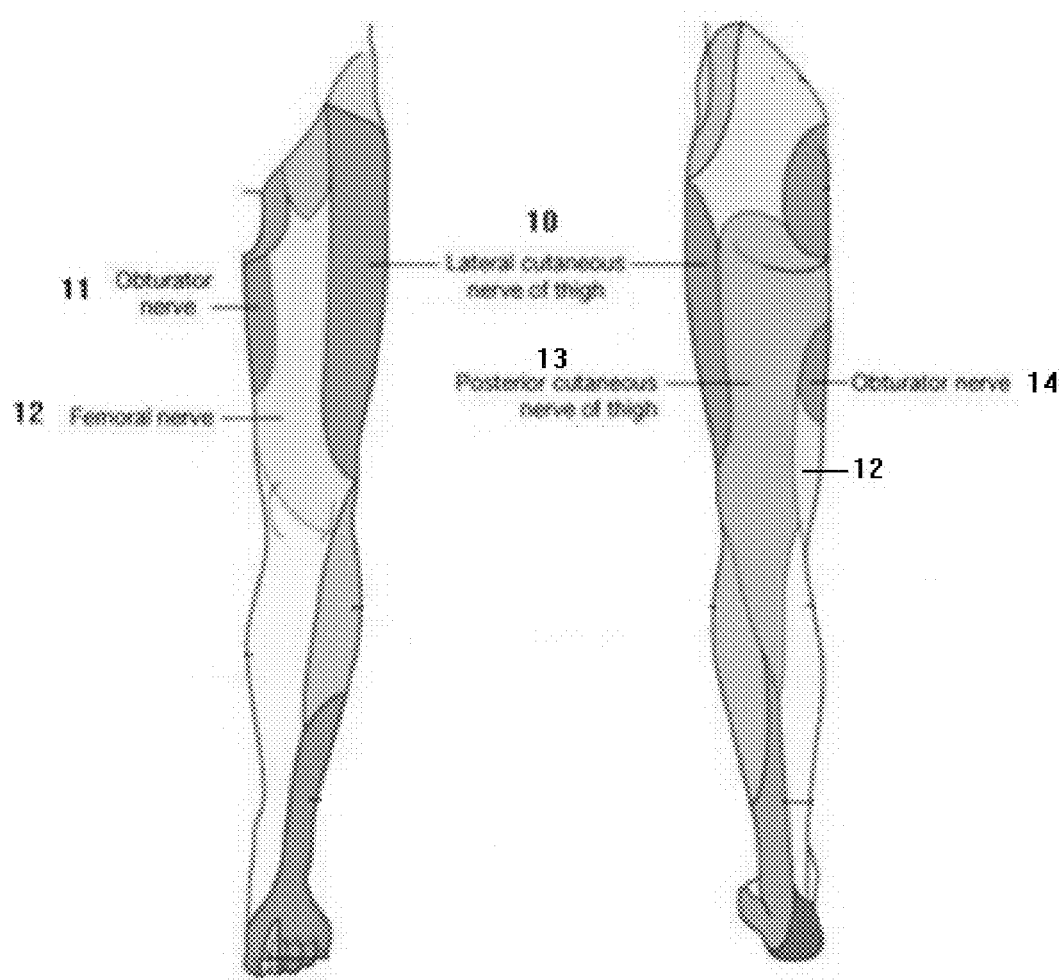

FIG. 3. Dorsal thigh and upper leg surfaces on which output devices may be arranged.

Figure 4:
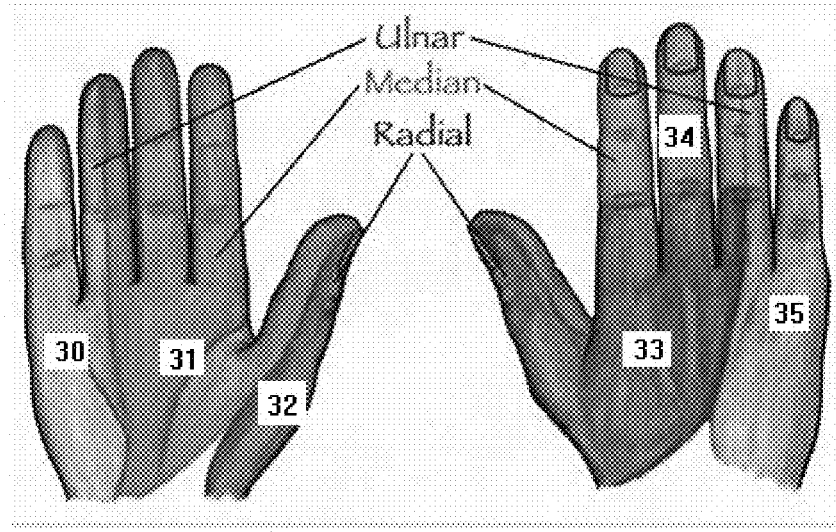

FIG. 4. Hand and finger surfaces on which output devices may be placed.

Figure 5:
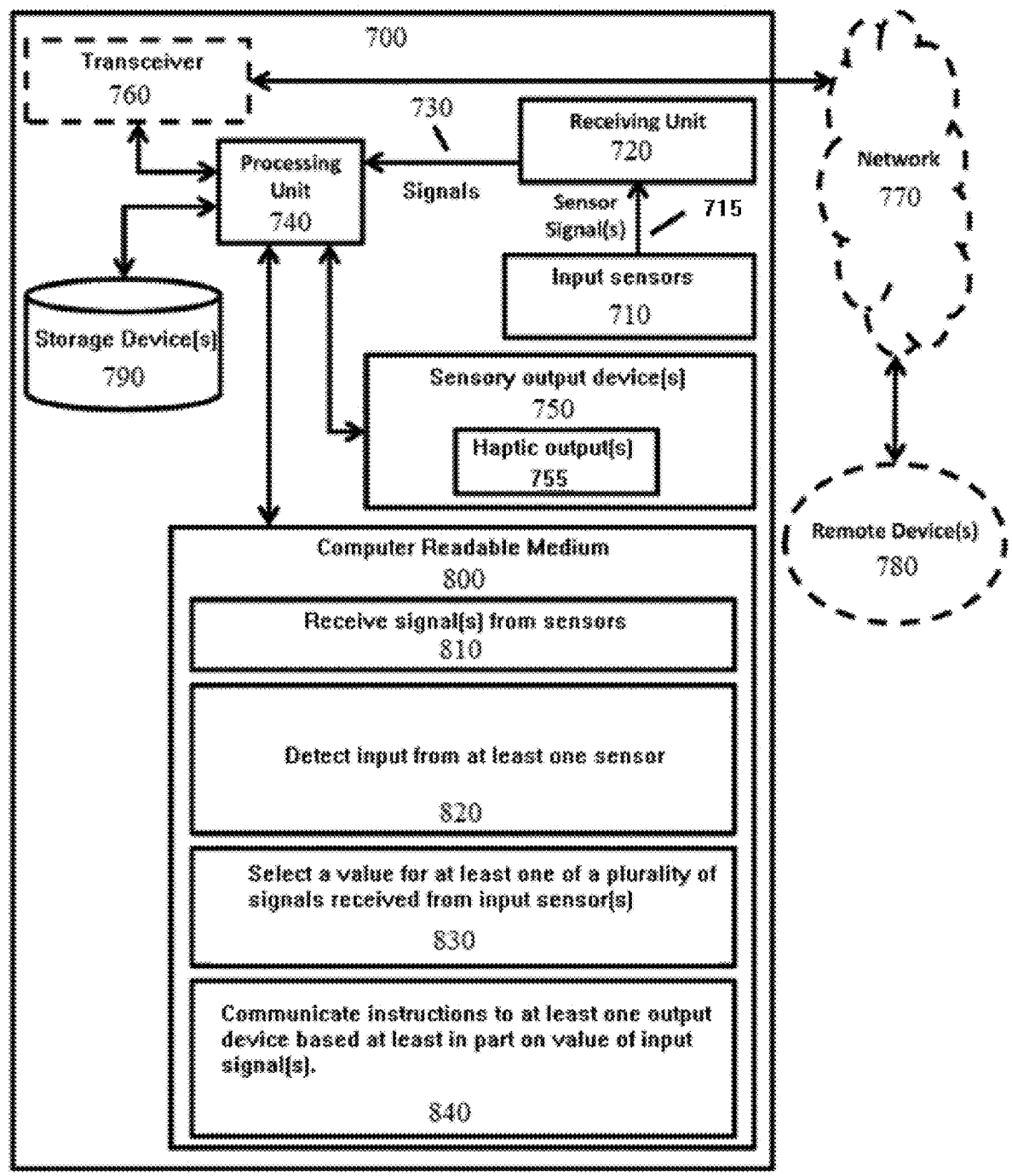

FIG. 5. Block diagram showing an interrelationship of the elements in one example of the invention. In a more basic form, input sensors (710) are connected to processing unit (740) and to sensory output devices (750).

DETAILED DESCRIPTION OF THE INVENTION

Users.

A user of the system or device as described herein generally is not able to directly perceive sensations signaling injury or a risk of injury due to a loss of sensation in the lower limbs or in portions of the lower body such as the feet and ankles. The loss of sensation leads to an increased risk of injury from abrasions, cuts and puncture wounds, neuropathic ulcers, pressure ulcers, diabetic foot syndrome, and other trauma because objects causing such injury are not felt. The presence of small stones or other abrasive, cutting, puncturing or blistering objects is not detected leading to injury. An individual with diminished or loss of lower body sensation may also be incapable of detecting whether the foot is too hot or too cold resulting in risk of burn or freezing injury or ischemic injury due to loss of circulation.

Loss of sensation makes it difficult for a person to detect the position of a foot or ankle, such as whether a foot is level with the ground or whether it is firmly supported by a surface thereby increasing the risk of a fall.

Individuals with a loss of sensation in the feet and lower limbs include those with diabetes or diabetic neuropathy, alcoholism including chronic alcohol abuse, Charcot-Marie Tooth disease, frostbite, stroke, crushing or other physical injuries, Guillan-Barré syndrome, herniated disks, Lyme disease, Morton's neuroma, multiple sclerosis and loss of sensation associated with chemotherapy, radiation exposure, spinal cord injury, and vasculitis. These subjects can particularly benefit from using the system and device of as disclosed herein.

Device/System.

A wired device and/or system with at least one wireless connection as described herein compensates a user for lost sensation in the foot, ankle or lower limb. This is accomplished by incorporating one or more sensor inputs on and around the foot, ankle and lower limb that detect pressure, punctures, weight, moisture, conductance, temperature, including skin temperature, and positional signals and convey these signals to the user, for example, by an output of tactile signals on the user's thigh or other bodily surface that can perceive the tactile signals.

In one embodiment as shown by FIG. 1 the device will include input pressure sensors on the foot, ankle or lower limbs (100) linked via a processor (300) to output devices (400) on the thighs or another sensate body surface. Positioning the output devices for each foot on separate thighs permits the user to easily discriminate between signals received from separate feet. Similarly, output devices for each foot may be attached to skin surfaces on the right or left sides of the body. In some embodiments, output devices will be positioned on the front of the thighs, in others on the back of the thighs, and in still others on anterior, lateral, and/or posterior surfaces of the thigh, for example, sensors on the plantar surface of the foot may deliver signals to output devices on the posterior portion of the thighs and sensors on the dorsal surface of the foot can deliver signals to output devices on the anterior portion of the thighs.

Input Sensors.

Any type of input sensor suitable for attachment to the foot, ankle or lower limb may be selected depending on the habits, lifestyle and specific needs of the users. Typically, these sensors are removably attached, do not require surgical implantation, and do not damage the skin. Sensors can be worn under or around the foot, ankle or lower limbs and include piezoresistive, piezoelectric, capacitive and elastoresistive sensors as well as arrays of pressure sensors, strain gauge rosettes, and biologically inspired sensors. Any number of input sensors may be mounted on the foot, ankle or lower limb as necessary to provide input needed by a particular user. For example, 1, 2, 3, 4, 5, 6, 7, 8, 9, 10 or more input sensors, sensor arrays or sensor grids, may be placed on or around the foot, ankle or lower limb. Fewer sensors may be used for a subject with partial or limited neuropathy.

Any type of input sensor may be employed. Preferably the device includes or is based on the use of pressure sensors which indicate an amount of pressure on a portion of a toe, foot or ankle, for example, to assist a user to determine whether a shoe is loose or tight or determine the amount of pressure or weight placed on different parts of the toe, foot, sole or ankle. Thus, a basic device may include pressure sensors placed on different portions of the foot such as the toe and heel or any or all of the portions of the foot innervated by the nerves described by FIG. 2. For example, input sensors that measure pressure may be placed on plantar surfaces 1, 4, 5, 6 and 7 and/or on dorsal surfaces 1, 2, 3 and 7 shown by FIG. 2.

In some embodiments, output devices are placed on either the front or rear skin of the thighs. These output devices may be configured as a virtual foot surface A or B as shown by FIG. 1. Output devices are placed in positions within surfaces A or B that correspond to placement of input sensors on the right plantar surface (sole) of the foot and/or dorsal surface of the foot. Reflected symmetrical areas A' and B' (not shown) can be imposed on the left thigh which corresponding to sensor inputs from the left foot.

Output device placement using virtual area A and A' has the advantage of aligning area A with the right foot below it and area A' with the left foot below it. Output device placement using virtual area B and B' has the advantage of aligning sensory input from sensors at the distal part of the feet with the upper, generally wider, part of the thigh.

is apart enough to be sensed by 2 branches of the sensing nerve. For example to distinguish tow points of pressure in the same innervated area should be different in the force so that the nerve will feel them, or there should be an enough distance that different branch of the nerve is innervating these different 2 areas, so it is sensed as 2 stimuli. This area to discriminate 2 points of sensation differ from one part of the body to another, it is more accurate in distal parts than proximal, for example the tip of fingers are most sensitive part to 2 point discrimination and this area become bigger as we go proximal for the arm for example.

| Input sensor | Output devices Thigh (A, virtual toe down) | Output devices Thigh (B, virtual toe up) | Output devices on Hand |
| --- | --- | --- | --- |
| Dorsal surface of foot | Location of output device: (front thigh) | Location of output device: (front of thigh) | Location of output device: dorsal surface of hand |
| 1 | 10, 12, 13 | 11, 12 | 33, 34, wrist |
| 2 | 10, 12 | 12 | 34 |
| 3 | 10, 11, 12 | 10, 11, 12 | 33, wrist |
| 7 | 11, 12 | 10 | 35 |
| Location of input sensor (plantar) | Location of output device (rear of thigh) | Location of output device (rear of thigh) | Location of output device: palmar surface of hand |
| 1 | 12, 14 | 11, 12 | 31, 32 |
| 4 | 12, 13, 14 | 13 | 31, 32 |
| 5 | 10 | 10 | 30 |
| 6 | 13 | 12, 13 | Proximal portions of 30, 31, 32, or wrist |
| 7 | 10 | 10, 13 | 30 |

In other embodiments, output devices are placed on both the front and rear surfaces of the thighs, for example, where input sensors placed on the plantar surface (sole) of the foot activate output devices placed on the rear of the thigh and where input sensors placed on the dorsal surface of the foot activate output devices on the front of the thigh; or vice versa, where input sensors placed on the plantar surface (sole) of the foot activate output devices placed on the front of the thigh and where input sensors placed on the dorsal surface of the foot activate output devices on the rear of the thigh. In these embodiments, corresponding virtual foot outlines A and B appear on both the front and rear of the thighs. For example, virtual areas A and B as shown in FIG. 1 (or A' and B' on the left thigh) may extend to define both front and rear surfaces of the thigh.

Preferably, both input sensors and output devices are positioned over areas of the skin innervated by preselected nerves to facilitate localization of sensory inputs from the input sensors. The alignment of input sensor signals placed on areas of the foot innervated by particular nerves with areas of thigh innervated by particular nerves in the thigh will depend on whether virtual foot configuration A or B (or A' or B') is selected.

Linkage between input sensors positioned over areas of skin on the foot innervated by particular nerves and areas of skin on the thighs or hands innervated by particular nerves may be based on approximate anatomical correspondence between positions of the input sensors on the foot and areas. Some non-limiting examples of correspondence between input sensors and output devices on the hands and thighs are provided by the Table below. This linkage provide more accurate site of sensation correspondence, due to that anatomically innervated area feels the sensation of 2 points if it Those skilled in the art will recognize that input sensors and output devices may be further localized to corresponding subsections of the areas described by FIGS. 2, 3 and 4. For example, an input sensor on the big toe may be linked to an output device positioned on the thumb or an input sensor on the heel may be linked to an output device positioned on the proximal portion of the hand or on the wrist.

Providing anatomical correspondence based on natural innervation between the positions of the input sensors and the output devices, permits a user to more easily identify the location of input received from the foot.

Similarly, foot-shaped arrays of output devices on the thighs linked to a similar array of input sensors on the feet assist a user in easily identifying the location of input received by the sensors.

These input sensors detect pressure or other signals, such as temperature, weight and pressure, humidity, position, feet alignment, shoes tightness, etc. without piercing the skin or by direct or surgical linkage to a user's nervous system. For example, input sensors typically will not penetrate the subcutaneous tissue, dermis, or inner layers of the epidermis, such as the stratum basale the stratum spinsum or stratum granulosum, and preferably do not breach any sublayer of the epidermis, the outermost layer of skin. Such input sensors may be positioned directly on the outer surface of the skin and held in place by a wearable garment, wrap or patch which may optionally include an adhesive to facilitate attachment of the input sensor to a particular location on the skin. In many embodiments the removal of the input sensor affects the skin no more than removal of a bandage or adhesive bandage. Typically, when the input sensors are removed from the skin of a user they leave no pierced or damaged skin.

Pressure sensors include those built from conductive rubber, lead zirconate titanate (PZT), polyvinylidene fluoride (PVDF), PVDF-TrFE, FET, and metallic capacitive sensing elements.

Pressure sensors or other sensors designed to detect materials capable of puncturing or lacerating the feet may contain one or more sensitive layers that when partially or completed punctured or lacerated deliver a signal to an output device to warn the wearer of the danger of a puncture wound or laceration.

Biologically inspired input sensors include those which can detect vibration, force, moisture, and/or heat transfer. Input sensors may deliver a binary signal such as a signal that pressure, temperature, moisture or other parameter is above or below a preselected threshold or may deliver a signal proportionate to the signal received, for example, a signal that is progressively more intense with increasing pressure, temperature, moisture or other parameter detected by an input sensor. Input sensors include those described or referenced by https://en.wikipedia.org/wiki/Tactile_sensor (last accessed Feb. 5, 2019, incorporated by reference).

Input sensors can be selected that determine the relative pressure or compression on different parts of the foot thus avoiding blistering or loss of circulation in the toes, foot or ankles due to external pressure from too-tight shoes or other foot coverings.

Input sensors may be selected to recognize foot position, balance based on differential pressure patterns on the sole, foot position and misalignment or malposition of the foot with regard to the ankle and leg, for example, they provide input which the processor can interpret as whether the foot is level or in a position suitable for walking or standing. Positional sensors such as those used in body motion suits may be used. These sensors provide input that reduces the risk of a fall or sprain to the foot.

To facilitate recognition and discrimination among signals received from different parts feet, input sensors may be selectively placed on different foot, ankle or lower limb surfaces that in healthy individuals are innervated by different nerves. In a subject lacking sensation in the feet and lower limbs such placement reiterates natural reception of signals by the feet, ankles and lower body. Thus input sensors on the foot may be placed next to a foot surface enervated by the medial plantar nerve, the medial plantar nerve and the lateral plantar nerve, the by the medial plantar nerve, the lateral plantar nerve, the tibial nerve and/or the sural and saphenous nerves; see FIG. 2. Depending on the individual user's needs, input sensors may be placed on one or more foot surfaces innervated by these nerves and linked to corresponding positions on the thigh or other surface to which output devices are attached. In some embodiments, inputs from a surface innervated by a particular nerve in foot or lower limbs will be linked to thigh skin surfaces innervated by a particular nerve of the thigh, for example, input from a sensor on the sole of the foot innervated by the medial plantar nerve (4), can be delivered to an output device positioned on the thigh on skin innervated by the posterior ramus or rami (17) or the obturator nerve (19).

Signal Processing.

To facilitate signal delivery between input sensors and output devices such as devices that deliver a tactile signal to skin on a thigh, the system and device can include a signal processing unit or signal transducing unit to receive signals from input sensors and transmit them to output devices in a form that activates the output device. The processor may transform one type of signal received from an input sensor into another type of signal that an output device receives. As described in the Example, some embodiments of the invention also involve signal storage and/or computer processing and can include wireless transmission of a signal. The processing may involve sorting the sensation signals as ordinary or high risk signals that may cause risk of fall or potential for injury and alarm the user and instruct him accordingly.

Tactile or Other Signal Outputs.

Output devices include outputs which receive and output tactile sensations such as touch and force. Tactile interface devices can include vibration motors (e.g., eccentric rotating mass (ERM) devices), Linear Resonant Actuators (LRAs), piezoelectric devices, and/or any other suitable devices (and/or combinations thereof, such as hybrid devices incorporating both ERM and LRA elements). The device(s) can additionally or alternatively be operable to provide one or more of: auditory stimuli, electrical stimuli, visual signals or displays, and any other suitable form of stimulus, that alarming for risky positions of fall, and instructions that may help the user in different situations.

Typically, output devices are arranged in a familiar, logical, or recognizable pattern that helps the user identify the source of the sensor input, for example, the pattern of distribution of input sensors on a foot may correspond to a pattern of output devices on the thigh; see FIG. 1 at reference character (500) which shows a virtual foot which is superimposable on the surface of a thigh. In other embodiments output devices may be arranged in lateral bands which correspond to front-to-rear or rear-to-front (horizontal stripes), or side-to-side (vertical stripes) sensor placement on the foot, see reference character (410), from front-to-back or from side-to-side.

In a typical embodiment, the output devices are placed on or around the thighs in positions corresponding to similar positions on the foot. For example, pressure input sensors placed on a portion of the foot enervated by the medial plantar nerve (4) may transmit signals to output devices on the surface of the posterior portion of the thigh enervated by the posterior cutaneous nerve; and, pressure sensors on the sole innervated by the lateral plantar nerve (5) or sural nerve (7) may transmit signals to output devices posterior surface of the thigh enervated by the lateral cutaneous nerve; and, pressure sensors on the a dorsal portion of the foot enervated by the superficial peroneal nerve (3) or deep peroneal nerve (2) may transmit signals to output devices placed on an anterior surface of the thigh enervated by the femoral or lateral cutaneous nerve. Depending on the condition and preference of the user, any other correspondence between areas (1)-(7) in FIG. 2 and areas (10)-(14) in FIG. 3 or areas (30)-(35) in FIG. 4 may be to link sensor input signals to output devices.

In another embodiment, instead of delivering signals from input sensors to the thigh, these signals may be delivered to positions on the hand corresponding to foot surfaces, for example, by incorporating output devices into gloves containing tactile output devices. Linkage between foot surfaces innervated by particular nerves and hand surfaces innervated by particular nerves may be employed. Input sensors positioned on skin innervated by nerves identified by (4), (5) and (6) in FIG. 2 may be delivered to the hand on skin at positions (30), (31) and (32) which are respectively innervated by the ulnar, median and radial nerves. Similarly signals from input sensors on the dorsal surface of the foot in areas (3), (2) and (7) in FIG. 2 can be delivered to output devices on areas (33), (34) and (35) shown in FIG. 4. Signals from input sensors may be conveyed to output devices in gloves directly via wires, for example, wires embedded in a body suit or an undergarment that covers the body between the input sensors and output devices, or may be conveyed via wireless signals to a receiver in or adjacent to the gloves containing output devices. In some embodiments, both the input sensors and output devices are embedded in a stretchable or elastic garment that positions the input sensors over the desired areas of skin and also positions the output devices over corresponding areas of skin on the thighs or hands. The garment can link signals received from the input sensors to the output devices via one or two processors which may also be built into the garment or worn separately by the user, for example, worn around the calves of the leg as shown by FIG. 1. When two processors are used, they may independently process input signals from the right and left legs, respectively. In other embodiments, a single processor connected to input devices in both legs may be used.

Pressure sensors placed on a portion of the foot innervated by the medial plantar nerve (4) may transmit signals to output devices on the surface of the palm innervated by the median nerve, pressure sensors on the sole innervated by the lateral plantar nerve (5), calcaneal branch of the tibial nerve (6) or sural nerve (7) may transmit signals to output devices on a surface of the palm innervated by the ulnar nerve; and sensors on a dorsal portion of the foot innervated by the superficial peroneal nerve (3) or deep peroneal nerve (2) may transmit signals to output devices placed on a hand surface innervated by the radial nerve.

Other linkage schemes between surfaces of the foot innervated by the saphenous (1), deep peroneal nerve (2), superficial peroneal nerve (3), medial plantar nerve (4), lateral plantar nerve (5) calcaneal branch of the tibial nerve (6) and sural nerve (7) nerves and hand surfaces innervated by the ulnar, median and radial nerves may be selected based on the nature of the neurological deficit and the preference of a subject. Any other correspondence between areas (1)-(7) in FIG. 2 and areas (30)-(35) in FIG. 4 may be selected to link sensor input signals to output devices.

An output device may deliver a single type of signal, for example, a tactile output corresponding to the amount of pressure on a corresponding input sensor, or more than one type signal, for example, a tactile output indicating a degree of pressure on the input sensor as well as the amount of moisture, conductance or temperature on the input sensor. Output may be provided by a single output device that delivers one or more tactile output signals to the skin, for example, tactile outputs at different frequencies that correspond to qualitatively different sensor inputs such as pressure, temperature, moisture, etc. Alternatively, individual output devices that deliver tactile outputs dedicated to one type of sensor input, such as pressure or temperature but not both, may be arranged at the same, adjacent or different locations on the thigh or other skin surface.

Positional sensors on the foot alone or in combination with other positional sensors on the foot, may indicate whether the sole of the foot is level, the height of a foot with respect to the other foot, whether the foot is in motion or stationary, gait and length of stride, whether only part of the foot is in contact with a surface, or relative pitch, roll or yaw of a foot, such as the angle made by the toe and heel with respect to a surface, pronation or supination of a foot, or whether the foot exhibits in-toeing (pigeon toe). Position of a foot may be indicated by a tactile signal delivered via an output device or may be delivered visually or aurally, for example, by one or more flashing lights or alarms indicating when a foot is not level, not fully in contact with a surface or otherwise malpositioned. In some embodiments, wearable input sensors are used for gait event detection. These include footswitches (e.g. pressure insoles or force sensitive resistors), joint angle measurement sensors such as a potentiometer, goniometer or electromyography (EMG) sensors, and other inertial sensors such as accelerometers, gyroscopes and their combination which is known as an inertial measurement unit. Inputs from these sensors may be processed using a gait event detection algorithm to help a patient maintain a proper foot position and gait or correct an improper one.

In some embodiments, sensors such as those used in body motion suits may be incorporated into the device described herein. In some embodiments, the relative position of a foot may be transmitted to an output display such as to a wireless phone screen or a wearable computer having visual or aural output. In some embodiments, motion capture sensors may be used to provide positional information for a foot, ankle or lower limb.

Clothing.

In some embodiments, input sensors and output devices are embedded into a wearable form. Thus input sensors may be incorporated into a sock or sock-like covering which can surround all surfaces of the foot including the sole, the sides of the foot and the top surfaces of the foot and ankle. In other embodiments, this sock-like portion may be part of an integrated garment that also covers the thighs or other parts of the body and contains tactile output devices, such as leggings, body wrap, leotards, unitard, unisuits, Zentai suits, compression garments, wetsuits, skinny jeans, slacks, yoga pants, foundation garments, motion capture suits, hosiery, support hose, swimwear, underwear, or other close-fitting clothing that covers the feet, ankles and/or thighs and brings these surfaces into contact with input sensors or tactile output devices. In some embodiments, such as that depicted by FIG. 1 the input sensors and output devices may be incorporated into separate pieces of clothing, such as into socks or foot coverings and into clothing that fits around the thighs. A processing device is preferably placed between the input sensors and the output devices as also shown by FIG. 1 and may be incorporated into clothing or worn on the calves, legs or other parts of the body. In some embodiments input sensors will deliver signals to output devices in gloves or to local or remote displays or devices. Wearable devices and clothing may contain stretchable fabrics such as Spandex® (elastane) and Spandex® blends which are known and incorporated by reference to https://_sewguide.com/stretchy-fabric/ or https://_en.wikipedia.org/wiki/Spandex (each last accessed Feb. 7, 2019).

Specific embodiments of the invention include, but are not limited to the following:

A device mounted on a human leg comprising a power source and at least one input pressure sensor, operably connected to at least one processor, operably connected to at least one output device that delivers a tactile signal to the skin or an audible alarm or visual display, wherein the device is configured so that the at least one input pressure sensor is adjacent to skin on the foot or ankle and so that the at least one output device is adjacent to skin on the thigh or wherein the output device produces an auditory warning or visual display. This device may be configured to position the at least one input pressure sensor on the dorsal surface of a foot or configured to position the at least one input pressure sensor on the plantar surface of a foot. Any portable power source may be incorporated into the device of the invention, including into a stretchable garment that contains the input sensors, processor and output devices and covers the feet and thighs or hands (or other parts of the body where output devices may be positioned). Portable power sources include batteries, such as alkaline or lithium batteries, stretchable batteries, and rechargeable batteries, fuel cells including those that use glucose, physiological fluids, and other biofuels, photovoltaic or RF harvesters including those that harvest body heat, supercapacitors, and solar cells.

The device can include multiple input pressure sensors positioned to be adjacent to at least three, four, five, six or seven different surfaces of the foot innervated by different nerves. More than one input sensor may be placed in an area of skin innervated by a particular nerve.

It can include at least one input pressure sensor positioned to be adjacent to a surface innervated by the saphenous nerve or adjacent to a surface innervated by the sural nerve. It can include input sensors on skin surfaces innervated by the medial plantar, lateral plantar, saphenous, sural and tibial nerves.

In some embodiments, the device will include at least one input sensor that detects a puncture or laceration of the sensor for example a sensor with multiple layers that detect the presence of a puncturing object. In other embodiments, the at least one input sensor will detect skin temperature or temperature, moisture of conductance around the food or ankle.

In other embodiments, sensors that detect foot or limb position such as whether a foot is inclined or level with a surface, motion of the foot or limb, or distribution of pressure on a foot when standing or striding.

The device may include at least one input sensor that detects an unsafe or risky foot position and an output device that emits an audible alarm or audible warning when the foot position is not level, not fully supported by a surface, or is otherwise abnormal. In some embodiments a visual indicator or display may also warn the user of an abnormal or unsafe foot position.

Many embodiments of this device will contain one or more output devices located or positioned on a body surface that does not suffer from lack of sensation such as on the thigh or thighs of a user. Generally, these output devices vibrate or provide other kinds of tactile signals to this skin surface. There is no limit to the number of output devices placed on the surface of the skin, for example, 1, 2, 3, 4, 5, 6, 7, 8, 9, 10 or more output devices may be positioned or array on a thigh or other body surface, preferably, in positions that map to the shape of the foot on which input sensors are placed. Individual output devices or arrays, rosettes or grids of output devices may be used.

In some embodiments, the device is configured to place at least one of the output devices on an area of the thigh innervated by the lateral cutaneous nerve or femoral nerve or configured to place at least one of the output devices on an area of the thigh innervated by the posterior cutaneous nerve.

The device as described herein may include one or more pieces of a stretchable fabric that alone or in combination cover the foot, ankle and thigh. For example, the individual sensors and output devices of the invention may be incorporated into an article of clothing.

Another embodiment of the invention is directed to a method for compensating for loss of sensation in a foot, ankle or lower limb of a human subject comprising clothing the subject with the device as disclosed herein. Such a human subject may be someone having has diabetic neuropathy or another disease, disorder or condition causing loss of sensation in the foot or lower limbs.

EXAMPLE

The device or system as disclosed herein is preferably one that receives one or more input signals from sensors on the foot, ankle or lower limbs, and provides stimuli through sensory output devices such as tactile interface devices positioned over an area of skin not substantially impaired by neurological deficit. It may optionally include one or more other elements besides input sensors, processor and output devices, including those described in the block diagram of FIG. 5. It may include power modules and other power sources, electrical or optical wiring or wireless communication modules.

The sensor inputs and other device components associated with the output devices are preferably disposed in a single device, but can additionally or alternatively be disposed as a system across a plurality of devices, and/or be disposed in any other suitable manner.

FIG. 5 is a block diagram showing one example (700) of the system of the invention for receiving input from sensor(s) placed on a foot, ankle or lower limb and receiving and processing these signals to output devices as described herein. In some embodiments system 700 may include at least one storage device 790 which can may store a plurality of sensor input and signal output parameters. The at least one storage device 790 may be a volatile or non-volatile memory device, such as RAM, ROM, EEPROM, or any other device capable of storing data.

The system 700 includes at least one input sensor 710 and preferably more than one input sensor, for example, sensors placed on dorsal or plantar surfaces of a foot lacking sensation or on surfaces which in a healthy subject are innervated by different nerves as shown by FIG. 2. The at least one input sensor 710 may measure at least one tactile or other sensory parameter such as pressure, weight, edema, blood circulation, temperature, skin temperature, moisture or conductance, and foot, ankle or limb position. The system 700 typically includes receiving unit 720 which can receive at least one signal 715 from the input sensors 710. Each of the at least one input sensor signals 715 may be communicated from one of the at least one input sensors 710. Alternatively, the receiving unit 720 may include at least one transceiver that communicates with at least one of the input sensors 710. The receiving unit may receive signals from 2, 3, 4, 5, 6 or more input sensors 710 placed at different positions on the body, such as over foot surfaces enervated by different nerves. In other embodiments, the receiving unit will receive signals from different types of input sensors, such as from weight, pressure, position, moisture, or temperature sensors placed at the same or different positions on the foot, ankles or lower limbs.

According to an example of the present disclosure, the system 700 may include at least one sensory output device 750. Each of the at least one output devices 750 may deliver a sensory output 755 that can be felt or otherwise detected by a person wearing the device or elements of the system. Thus, each of the output devices 750 can provide an output that can be detected by the wearer, such as a tactile sensation, an auditory signal such as a ringtone on a wireless phone or beeper, or visual output such as a light or series or array of lights, or a display on a screen such as a wireless phone screen.

Preferably from the standpoint of providing a tactile signal to restore loss of feeling in a foot, ankle or lower limb, the at least one output device 750 will deliver a tactile output to skin surfaces on a thigh or thighs of the user. These signals may be binary, such as a signal indicating pressure above or below a threshold value or may be proportionate to the signals received from the input sensors, such as a tactile output that increases with increased pressure on the input sensor or a vibrations of different frequencies indicating different degrees of pressure, temperature or moisture.

According to some of the various embodiments, the system 700 may include a processing unit 740 and a tangible non-transitory computer readable medium 800. The processing unit 740 may include at least one processor. As used herein, physical processor or processor refers to a device capable of executing instructions encoding arithmetic, logical, and/or I/O operations. In one illustrative example, a processor may follow Von Neumann architectural model and may include an arithmetic logic unit (ALU), a control unit, and a plurality of registers. In a further aspect, a processor may be a single core processor which is typically capable of executing one instruction at a time (or process a single pipeline of instructions), or a multi-core processor which may simultaneously execute multiple instructions. In another aspect, a processor may be implemented as a single integrated circuit, two or more integrated circuits, or may be a component of a multi-chip module (e.g., in which individual microprocessor dies are included in a single integrated circuit package and hence share a single socket). A processor may also be referred to as a central processing unit (CPU). In an example, the one or more physical processors may be in the system 700. In an example, all of the disclosed methods and procedures described herein can be implemented by the one or more processors. Further, the system 700 may be distributed over multiple processors, memories, and networks.

The computer readable medium 800 may include instructions that may cause the processing unit 740 to receive at least one signal 730 at block 810. The at least one signal 730 may be received from the receiving unit 720. The computer readable medium 800 may include instructions that may cause the processing unit 740 to detect an abnormal foot position, abnormal pressure, abnormal temperature or other abnormal signal input through employment of an estimation method at block 820. Abnormality is measured in relation to a signal an otherwise identical healthy subject who does not suffer from neural dysfunction in the lower limbs such as that caused by diabetes or other disability. The estimation method may be based at least in part on at least one of the input signals 730. The computer readable medium 800 may include instructions that may cause the processing unit 740 to select a value for at least one of the parameters at block 830. The value may be based at least in part on at least one of the at least one input signal 730. The computer readable medium 800 may include instructions that may cause the processing unit 740 to communicate instructions to at least one of the at least one output device 750 at block 840, such as calibration, sensitivity, or reset instructions. These instructions may be based at least in part on the intensity of inputs from the input sensors.

According to some of the various embodiments, the system 700 may include a transceiving unit 760 that includes at least one transceiver that includes at least one transmitter and at least one receiver. For example, the transceiving unit may transmit a signal received via the processor from a sensor input on the foot to a local or remote alarm or video display, such as on a wireless phone or wearable computer. At least one of the at least one receiver may be the same as at least one of the at least one receiver associated with the receiving unit 720. Alternatively, at least one of the at least one transceiver may be the same as at least one of the at least one transceiver associated with the receiving unit 720. The transceiving unit 760 may communicate with at least one remote device 275 employing network 770. By way of example and not limitation, the remote device 780 may be employed by the user, a remote operator, a medical professional, combinations thereof, and/or the like. The system 700 may accept operational instructions from the remote device 780. The system 700 may communicate notifications to the remote device 780. In an alternate example, transceiving unit 760 may be directly communicatively connected to remote device 780.

According to some embodiments, the at least one storage device 790 may be communicatively coupled to system 700 through employment of a wired and/or wireless network. The at least one storage device 790 may be managed through employment of a cloud service, a web-based electronic data capture system, a web application, a mobile device application, a mobile device operating system, a virtual machine, combinations thereof, and/or the like.

According to an example of the present disclosure, a sensor signal (715) and a signal (730) may be the same. Alternatively, a signal (730) may be the baseband signal contained within a sensor signal (715). In some embodiments, the processing unit (740) will calculate foot, ankle or limb position using signals received from sensors placed at different positions on the body, such as over different foot or ankle or limb surfaces and/or from signals received at different points in time, such as over the time period of a complete stride or series of strides.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A wearable foot sensory device, comprising:
a power source, one or more input pressure sensors that measure pressure, one or more processors, and one or more output devices;
wherein the one or more input pressure sensors are configured to be positioned on a dorsal surface of a foot or ankle of a wearer so that it is next to a preselected area of skin on the foot or ankle of the wearer when the device is worn,
wherein each of the one or more output devices is configured to be positioned so that it is next to a preselected area of skin on a thigh of the wearer when the device is worn, wherein the one or more output devices are configured to be positioned within a foot-shaped area on the thigh of the wearer and a position of each of the one or more output devices in the foot-shaped area correlates with a position of one of the at least one input pressure sensors, and
wherein the power source, the one or more input sensors, the one or more processors, and the one or more output devices are interconnected so that power is delivered to the one or more input sensors, the one or more processors, and the one or more output devices and so that signals received by the one or more input sensors are delivered to the processor and subsequently delivered to the one or more output devices, and
wherein at least one of the input pressure sensors outputs a signal and the processor determines if a puncture or laceration has occurred.

2. The device of claim 1, wherein the one or more input pressure sensors comprises at least four input pressure sensors configured to be positioned adjacent to at least four different surfaces of the foot innervated by different nerves.

3. The device of claim 1, wherein the device comprises at least one input pressure sensor configured to be positioned adjacent to a surface innervated by the saphenous nerve.

4. The device of claim 1, wherein the device comprises at least one input pressure sensor configured to be positioned adjacent to a surface innervated by the sural nerve.

5. The device of claim 1, wherein the one or more input pressure sensors are configured to be positioned adjacent to skin surfaces innervated by the medial plantar nerve, the lateral plantar nerve, the saphenous nerve, the sural nerve and the tibial nerve.

6. The device of claim 1, further comprising at least one input sensor that detects temperature.

7. The device of claim 1, further comprising at least one input sensor that detects moisture.

8. The device of claim 1, further comprising at least one input sensor that detects conductance.

9. The device of claim 1, further comprising at least one input sensor that detects a foot position.

10. The device of claim 1, wherein at least one of the one or more input sensors detects a foot position and wherein at least one of the one or more output devices produces an audible alarm or a visible signal when the foot position is not level, not fully supported by a surface, or is otherwise abnormal.

11. The device of claim 1, wherein the at least one of the one or more output devices are configured to provide a vibration or other tactile signal to the skin on the thigh.

12. The device of claim 1, wherein the device is configured to place at least one of the one or more output devices on an area of the thigh innervated by the lateral cutaneous nerve or femoral nerve.

13. The device of claim 1, wherein the device is configured to place at least one of the one or more output devices on an area of the thigh innervated by the posterior cutaneous nerve.

14. The device of claim 1 that comprises one or more pieces of a stretchable fabric that alone or in combination are configured to cover the foot, ankle and thigh.

15. The device of claim 1, wherein each component of the device and wires connecting the components together are incorporated into an article of clothing.

16. A method for compensating for loss of sensation in a foot, ankle or lower limb of a human subject comprising providing the article of clothing of claim 15 and activating it to convey signals from at least one of the one or more input sensors to at least one of the one or more output devices.

17. The method of claim 16, wherein the subject has diabetic neuropathy.

* * * * *